(12) United States Patent
Elmer et al.

(10) Patent No.: US 10,888,284 B2
(45) Date of Patent: Jan. 12, 2021

(54) ANGLED SLIT DESIGN FOR COMPUTED TOMOGRAPHIC IMAGING OF ELECTRON BEAMS

(71) Applicant: LAWRENCE LIVERMORE NATIONAL SECURITY, LLC, Livermore, CA (US)

(72) Inventors: John W. Elmer, Danville, CA (US); Alan T. Teruya, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 16/571,480

(22) Filed: Sep. 16, 2019

(65) Prior Publication Data

US 2020/0297290 A1    Sep. 24, 2020

Related U.S. Application Data

(60) Provisional application No. 62/821,594, filed on Mar. 21, 2019.

(51) Int. Cl.
*A61B 6/03* (2006.01)
*G01R 19/00* (2006.01)

(52) U.S. Cl.
CPC .......... *A61B 6/035* (2013.01); *G01R 19/0061* (2013.01); *G01N 2223/419* (2013.01); *H01J 2237/24542* (2013.01); *H01J 2237/28* (2013.01)

(58) Field of Classification Search
CPC ............... A61B 6/035; G01R 19/0061; G01N 2223/419; H01J 2237/24542; H01J 2237/28
See application file for complete search history.

(56) References Cited

U.S. PATENT DOCUMENTS

| | | |
|---|---|---|
| 6,300,755 B1 | 10/2001 | Elmer et al. |
| 8,791,426 B2 | 7/2014 | Elmer et al. |
| 9,105,448 B2 | 8/2015 | Elmer et al. |
| 9,535,100 B2 | 1/2017 | McAninch et al. |

*Primary Examiner* — Nicole M Ippolito
*Assistant Examiner* — Hanway Chang
(74) *Attorney, Agent, or Firm* — Eddie E. Scott

(57) ABSTRACT

Computed tomographic method and apparatus includes an electron or ion beam having a beam axis, a refractory metal disk; at least one slit in the refractory metal disk that receive the beam, wherein the slit is at an angle to the beam axis; a beam entrance opening in the slit that allows the beam to enter; an effective beam exit opening in the slit that allow the beam to exit, wherein the beam effective exit opening is smaller than the beam entrance opening; and a system for moving the beam across the refractory metal disk, wherein the beam enters the slit through the beam entrance opening and exits the slit through the effective beam exit opening; and a computed tomographic device for measuring the beam that enters and exits the slit for analyzing the beam.

20 Claims, 8 Drawing Sheets

ANGLED SLIT DESIGN FOR COMPUTED TOMOGRAPHIC IMAGING OF ELECTRON BEAMS

CROSS-REFERENCE TO RELATED APPLICATIONS

The application claims priority to and benefit under 35 U.S.C. § 119(e) of U.S. Provisional Patent Application No. 62/821,594 filed Mar. 21, 2019 entitled "Angled Slit Design for Computed Tomographic Imaging of Small Diameter Electron Beams," the content of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to tomographic imaging of electron beams and more particularly to an angled slit system for computed tomographic (CT) imaging of electron beams.

State of Technology

This section provides background information related to the present disclosure which is not necessarily prior art.

Enhanced Modified Faraday Cup (EMFC) currently uses a refractory metal disk with small slits in it to profile and analyze electron beams. The inventors' previous work has used slits measuring approximately 100 microns wide cut into the refractory metal disk using an electro discharge method. These slits allow beams with diameters several times larger than 100 microns to be analyzed, but complications arise when trying to measure smaller diameter beams where the entire beam would pass through the slit. Manufacturing slits in relatively thick refractory metals with smaller widths than 100 microns is not economically feasible, and the new method detailed below allows the slit, e.g. 100 micron slit, to have an effectively smaller width when placed at an angle relative to the electron beam. This allows a 100 micron slit, for example, to analyze beams with diameters less than 100 microns. In principle, there is no lower limit on beam diameters that can be measured with Applicants' new apparatus, systems and methods.

U.S. Pat. No. 6,300,755 for an enhanced modified faraday cup for determination of power density distribution of electron beams provides the state of technology information reproduced below.

"An enhanced modified Faraday cup (MFC) for fast determination of the power density distribution in non-circular and irregular electron beams involves an improvement of the MFC of the system for tomographic determination of power distribution in electron beams disclosed in U.S. Pat. No. 5,583,427 and improves the electron capture problem of this prior MFC. A method orients the measured beam profile with respect to the welding chamber when measuring non-circular electron beams. The enhanced MFC of this invention broadly involves several modifications, including: (1) enlarging one slit in the refractory metal disk, (2) providing a second slit disk located inside the Faraday cup, (3) a ring located below the second slit disk, (4) a beam trap located below the ring, and (5) improved grounding of the refractory metal disk. By making one slit in the refractory metal disk twice as wide as the other slits, more of the electron beam current passes through the wide slit and into the Faraday cup, which produces a larger signal at this location, and by placing the wide slit in the chamber at a known location, the reconstructed beam profile can be determined with the proper orientation. By providing a second slit disk inside of the Faraday cup, and which may be composed of copper, for example, the second disk provides a shield to eliminate the majority of the secondary electrons and ions from leaving the Faraday cup. The slits in the second disk are the same size as the outer disk, with one slit enlarged, and the slits in the two disks are aligned. By positioning a ring, such as made of graphite, below the second slit disk, it helps minimize the amount of secondary electrons and ions from being produced. By adding a beam trap below the ring, such provides even more containment of the electron beam when full beam current is being examined through the center hole of the MFC. To improve grounding of the outer (refractory metal) slit disk, a wire, such as tantalum, is brazed to the outer slit disk and then attached to the heat sink body, constructed of copper for example. Also, a clamp, such as copper, is employed to maintain pressure on the outer slit disk and thus maintains good electrical contact with the heat sink body."

U.S. Pat. No. 9,105,448,755 for an electron beam diagnostic system using computed tomography and an annular sensor provides the state of technology information reproduced below.

"The present invention provides a new concept for analyzing electron beams that uses an annular sensor rather than the multiple radial slit sensor (For example, the 17 radial slit prior art sensor) used in previously electron beam diagnostic systems. The annular sensor changes the geometry by which the electron beam is scanned over the sensor and has key advantages over the previously invented enhanced modified Faraday cup designs. These advantages include: 1) The annular sensor has no limitations on how many different electron beam profiles can be taken, which increases the resolution of the computer tomographically reconstructed electron beam profile, 2) the annular sensor allows the beam to be swept in a linear fashion rather than in a circular fashion across the sensor which is easier for many machines perform, 3) the beam can be analyzed without having to be swept as far away from the central location, which makes the diagnostic smaller and easier to use on most electron beam machines, and 4) the design can easily be incorporated with a detached heat sink which makes it simpler and easier to manufacture, particularly when used for higher power applications."

"An annular electron beam diagnostic sensor designed in a number of ways, but all embodiments rely on a circular shaped sensor, that can be continuous or segmented, and is arranged coaxially with the propagation axis of the electron beam. The basic principal is to sweep the electron beam over the sensor at a known speed using the standard magnetic deflection coils that are present on all electron beam welders, and on other electron beam devices such as scanning electron microscopes. As the beam crosses the sensor, the beam's current is intercepted, generating a current versus time profile of the electron distribution in the beam. The current in this signal is then measured, using a fast acting data acquisition system, to render a current versus position of the electron beam that is integrated along the length of the portion of the sensor that is intercepting the beam."

"By making the width of the annular sensor small relative to the size of the beam, and sampling the data rapidly, an accurate measurement of the beam's profile can be made. This process is repeated by scanning the beam at different angles over the sensor while keeping the beam scan direction normal to the tangent of the annular sensor. Each angle gives a different view of the beams profile which can be analyzed using CT methods to recreate the power density distribution in the beam.'

"The present invention has use in electron beam welding, electron beam gun design, focusing of high power electron beams, quality control of electron beams, high resolution profiling of electron beams, transferring electron beam parameters between machines and facilities."

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

This application discloses an improvement in the slit-disk design used for analyzing electron beams with the Enhanced Modified Faraday Cup (EMFC) or similar devices. The improvement comprises of a new angled slit design whereby the slit walls are not oriented parallel to the electron beam being measured. The improvement can be used in both the radial slit method such as that described in U.S. Pat. No. 6,300,755 and the annular slit sensor method described in U.S. Pat. No. 9,105,448.

This application discloses a computed tomographic apparatus. The apparatus includes an electron or ion beam having a beam axis, a refractory metal disk; a multiplicity of slits in the refractory metal disk that receive the beam, wherein the slits are at an angle to the beam axis; beam entrance openings in the slits that allow the beam to enter; effective beam exit openings in the slits that allow the beam to exit, wherein the beam effective exit openings are smaller than the beam entrance openings; and a system for moving the beam across the refractory metal disk, wherein the beam enters the slits through the beam entrance openings and exits the slits through the effective beam exit openings; and a computed tomographic device for measuring the beam that enters and exits the slits for analyzing the beam.

This application also discloses a computed tomographic method of analyzing an electron or ion beam. The method includes the steps of providing an electron or ion beam, wherein the beam has a beam axis; providing a refractory metal disk; providing a multiplicity of slits in the refractory metal disk that receive the beam, wherein the slits are at an angle to the beam axis; providing beam entrance openings in the slits that allow the beam to enter; providing effective beam exit openings in the slits that allow the beam to exit, wherein the beam effective exit openings are smaller than the beam entrance openings; moving the beam across the refractory metal disk, wherein the beam enters the slits through the beam entrance openings and exits the slits through the effective beam exit openings; and using a computed tomographic device for measuring the beam that enters and exits the slits for analyzing the beam.

Beams Smaller Than Slit Width—The new angled slit design provides an effective slit width that is smaller than the actual slit, allowing for the measurement of smaller beams than were previously possible when the analyzing slit walls were oriented parallel to the electron beam path. As before, the electron beam profiles and waveforms created by the angled slits are coupled with computed tomography to reconstruct and analyze the power density distribution in high power electron beams often used for welding. The improvements made here not only allow for the measurement of smaller beam diameters than previously possible, but also allow the slit disk to be manufactured more economically, and to provide higher resolution of the reconstructed results at the same time.

The inventors' application discloses apparatus, systems and methods for measuring the power density distribution of high power electron beams is essential for quality control in welding and other electron beam processing techniques. The inventors' application discloses apparatus, systems and methods improved slit resolution allows for the measurement of smaller diameter beams than were previously possible, which is essential for its application to newly developed electron beam technology that can focus electron beams to smaller diameters that were possible in the past.

Beams Larger Than Slit Width—The Inventors' new angled slit design also provides improved apparatus, systems, and methods for the measurement of beams that are larger than the width of the slit when the analyzing slit walls were oriented parallel to the electron beam path. In the prior art, when the electron or ion beam is larger than the width of the slit, the slit captures only a portion of the beam. The beam is wider than the slit and only a portion of the beam passes through slit. The Inventors' improved apparatus, systems, and methods provides an effective slit width that is smaller than the actual slit. The improvement comprises of a new angled slit design whereby the slit walls are not oriented parallel to the electron beam being measured.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1A:
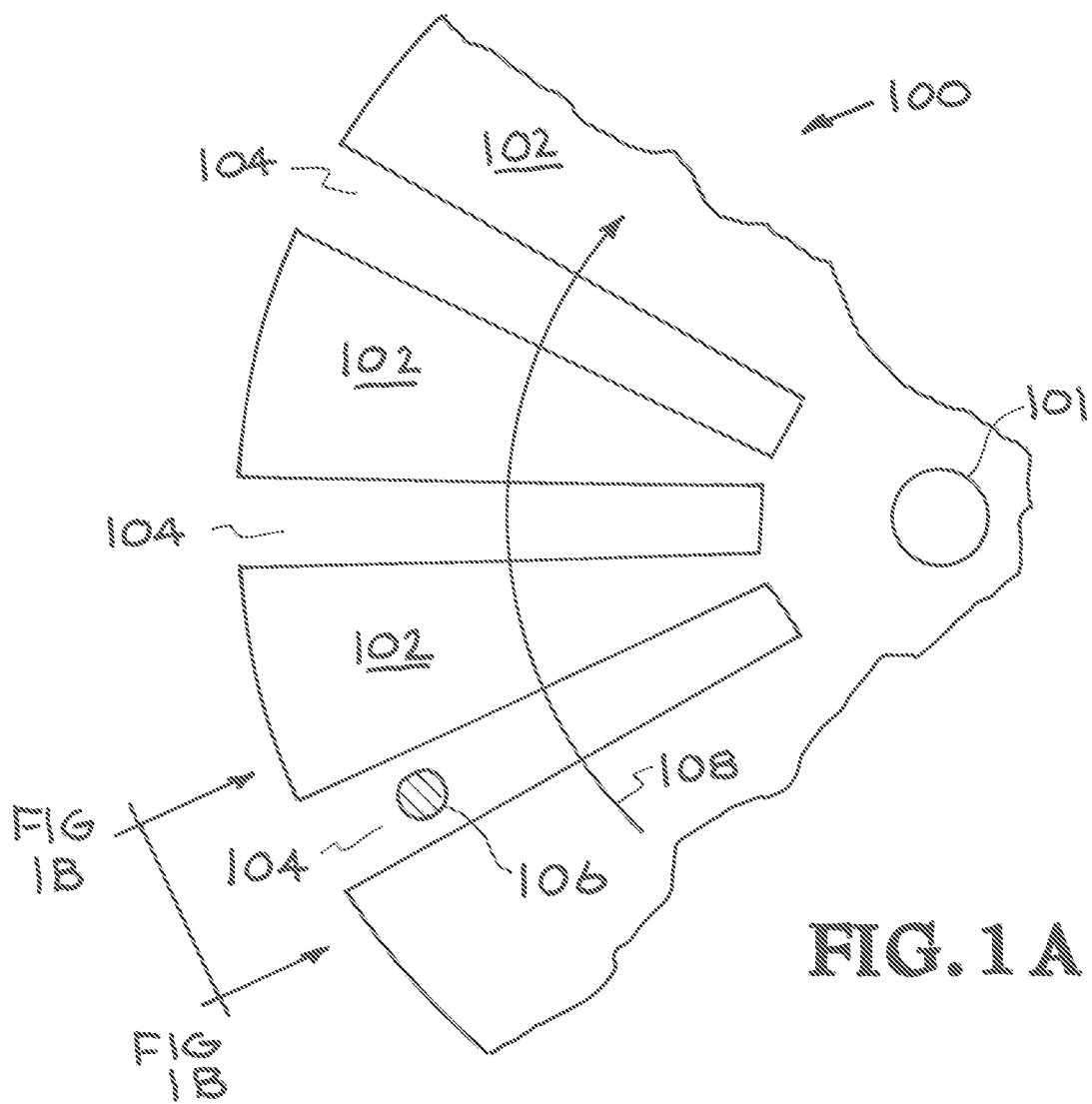
FIG. 1A provides background information for the present invention.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Referring now to the drawings and in particular to FIG. 1A, information is provided to serve as background for the description of the present invention. FIG. 1A illustrates a system for tomographic imaging of small diameter electron beams designated generally by the reference numeral 100. The system 100 includes a refractory metal disk 102, constructed preferably of tungsten, but may be constructed of tantalum, tungsten-rhenium, or other refractory metals. Disk 102 is provided, with a center hole 101 and a number (usually odd) of individual slits 104 extending radially outward from center hole 101 but spaced from the center hole. The number of slits is restricted by the allowable spacing of the slits. An electron or ion beam 106 travels in circular path 108 around the disc 102 and as the beam 106 crosses the slits 104 a signal is generated. This signal goes to a data acquisition system where an image of the current density in high or low power ion or electron beams is created. The number of data points taken is limited to the spacing of the slots.

The system 100 for tomographic imaging of small diameter electron beams illustrates the condition where a small diameter beam 106 is passing over a slit 104 that is wider than the beam 106. The beam 106 passes entirely through the slit 104. This complicates the computed tomographic (CT) reconstruction and reduces the resolution of the computed results. Significant errors are generated if the slit 104 is more than 50% the width of the beam 106.

A possible solution would be to provide finer slits 104. Producing finer slits in refractory metals would have an advantage in that smaller beams could be analyzed, and the spatial resolution of the CT reconstruction would be improved for all measured beams. However, there is a practical limitation on how fine a slit can be manufactured in a refractory metal disk, and slits smaller than 100 microns tend to be either cost prohibitive or not possible at all. Applicants' apparatus, systems, and methods solves this problem by manufacturing the slits of normal width, but oriented at an angle to the path of the electron beam that is being measured.

Figure 1B:
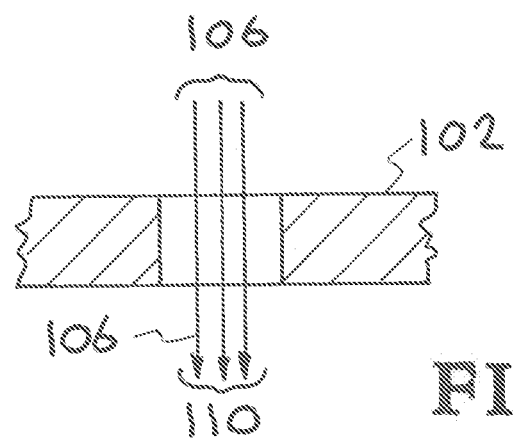
FIG. 1B is a cross-section of a section of one of the slits of the disk shown in FIG. 1A.

FIG. 1B is a cross-section of a section of one of the slits 104 of disk 102 shown in FIG. 1A looking radially downward. FIG. 1B illustrates the condition where a small diameter beam is passing over a slit that is wider than the beam. Newer machines generate finer beam diameters and as shown in FIG. 1B the diameter of beam 106 is smaller than the width of slit 104. Since the beam 106 diameter is less than the width of the slit 104, it allows the entire beam to pass through the slit. A system wherein the beam passing entirely through the slit complicates computed tomographic (CT) reconstruction and reduces the resolution of the computed results. Significant errors are generated if the slit is more than 50% the width of the beam.

The inventors' new apparatus, systems, and methods allow the slit, e.g. 100 micron slit, to have an effectively smaller width when placed at an angle relative to the electron beam. This allows a 100 micron slit, for example, to analyze beams with diameters less than 100 microns. In principle, there is no lower limit on beam diameters that can be measured with Applicants' new apparatus, systems and methods.

As illustrated in FIGS. 1A and 1B, as the beam 106 moves over the slit 104, a fast acting data acquisition system generates a profile of the distribution of current in the beam. By taking profiles over multiple radial slits, CT algorithms are used to calculate the power distribution in the beam. The inventors' new apparatus, systems, and methods provides an angled slit design with an effective slit width that is smaller than the actual slit, allowing for the measurement of smaller beams than were previously possible when the analyzing slit walls were oriented parallel to the electron beam path. As before, the electron beam profiles and waveforms created by the angled slits are coupled with computed tomography to reconstruct and analyze the power density distribution in high power electron beams often used for welding. The improvements made here not only allow for the measurement of smaller beam diameters than previously possible, but also allow the slit disk to be manufactured more economically, and to provide higher resolution of the reconstructed results at the same time.

Figure 2:
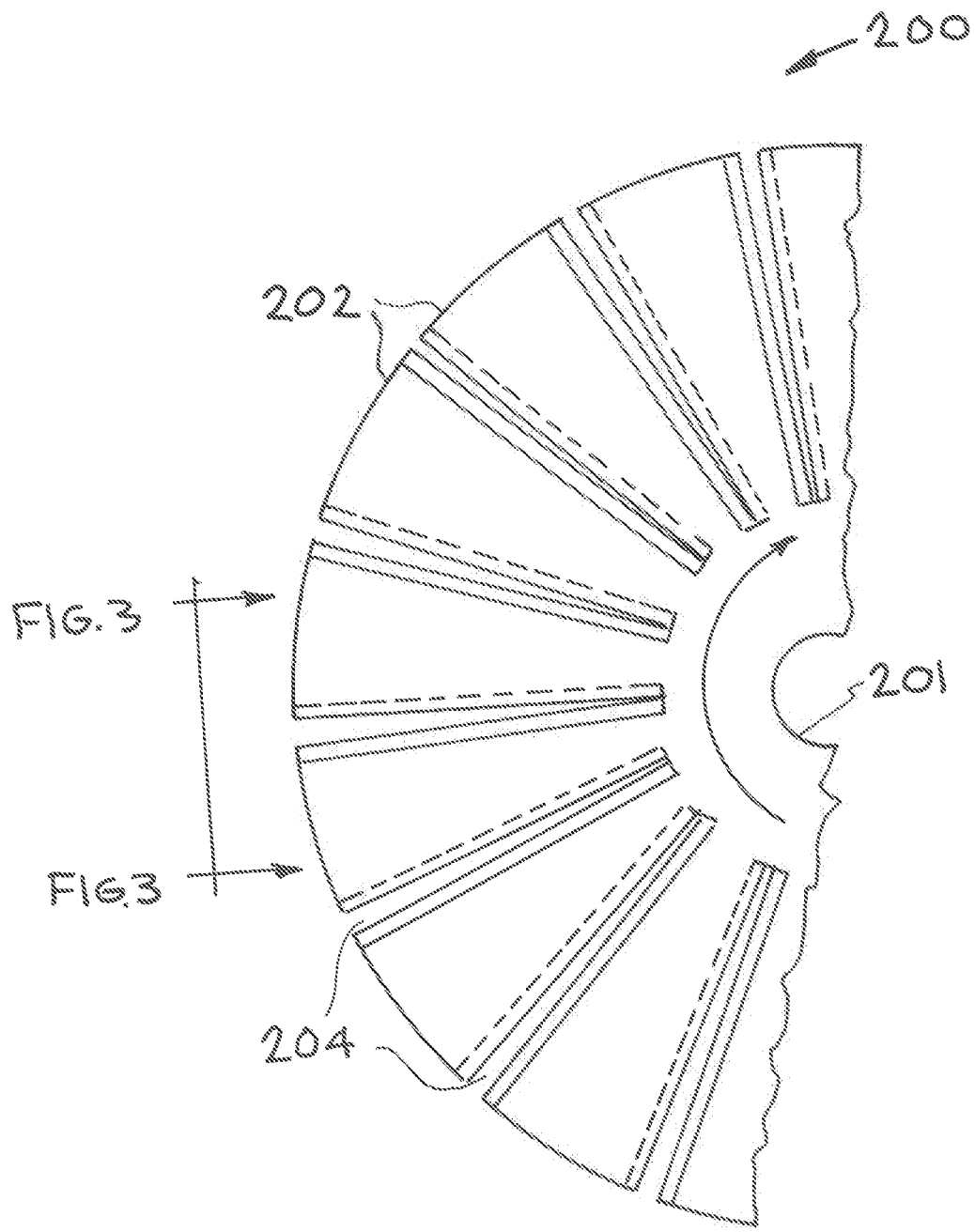
FIG. 2 is a simplified schematic depiction that illustrates a first embodiment of the inventor's apparatus, systems, and methods.

Referring now to the drawing and in particular to FIG. 2, a simplified schematic depiction illustrates a first embodiment of the inventor's apparatus, systems, and methods. This first embodiment is a system for tomographic imaging of small diameter electron beams. This first embodiment is designated generally by the reference numeral 200. As illustrated, the embodiment 200 includes a number of components. The components of the inventor's apparatus, systems, and methods 200 illustrated in FIG. 2 are identified and described below.

Reference Numeral 201—center hole,
Reference Numeral 202—refractory metal disk, and
Reference Numeral 204—slits.

The identification and description of the first embodiment 200 components illustrated in FIG. 2 having been completed, the operation and additional description of the inventor's first embodiment 200 will now be considered in greater detail. FIG. 2 provides an illustration of how an angled slit would work for a beam smaller than the width of the slit. The refractory metal disk 202 includes a center hole 201 and slits 204 that extend radially outward from center hole 201. The slits 204 are spaced from the center hole 201. By inclining the slits 204 at an angle the effective slit width is reduced to less than the slit width. The inclined slit is further illustrated in FIG. 3. The FIG. 3 view is taken as indicated by the arrows in FIG. 2.

Figure 3:
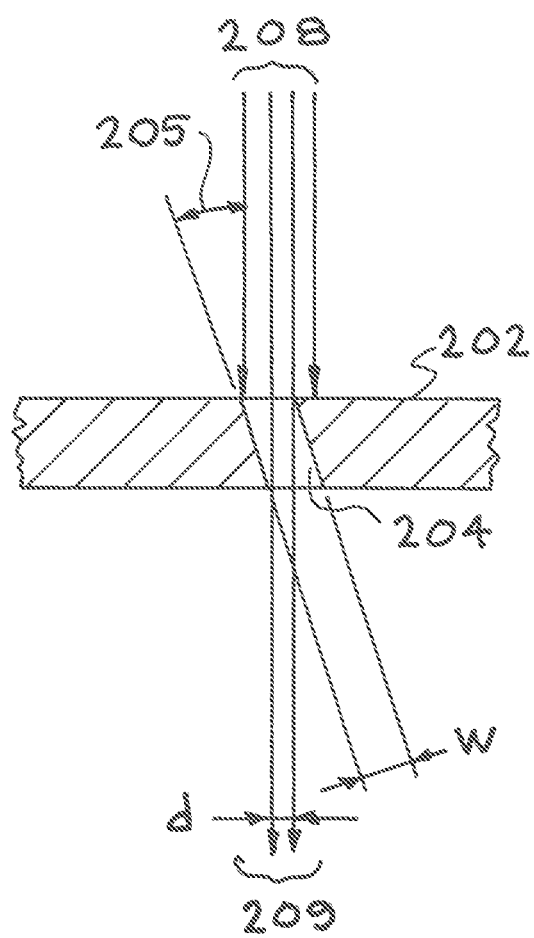
FIG. 3 is a view indicated by the arrows in FIG. 2.

Referring now to FIG. 3, is a view taken as indicated by the arrows in FIG. 2. The FIG. 3 view provides an illustration of the inventors' new angled slit 204 that provides an effective slit width that is smaller than the width of the actual slit 204. A portion of the refractory metal disk 202 is shown in FIG. 3 with the slit 204 extending through the metal disk 202. The slit 204 extends through the metal disk 202 at an angle 205 to the beam 208. By inclining the slit 204 at an angle the effective slit width is reduced to less than the slit width. This allows for the measurement of smaller beams than were previously possible when the slit walls were parallel to the electron beam path.

Figure 4A:
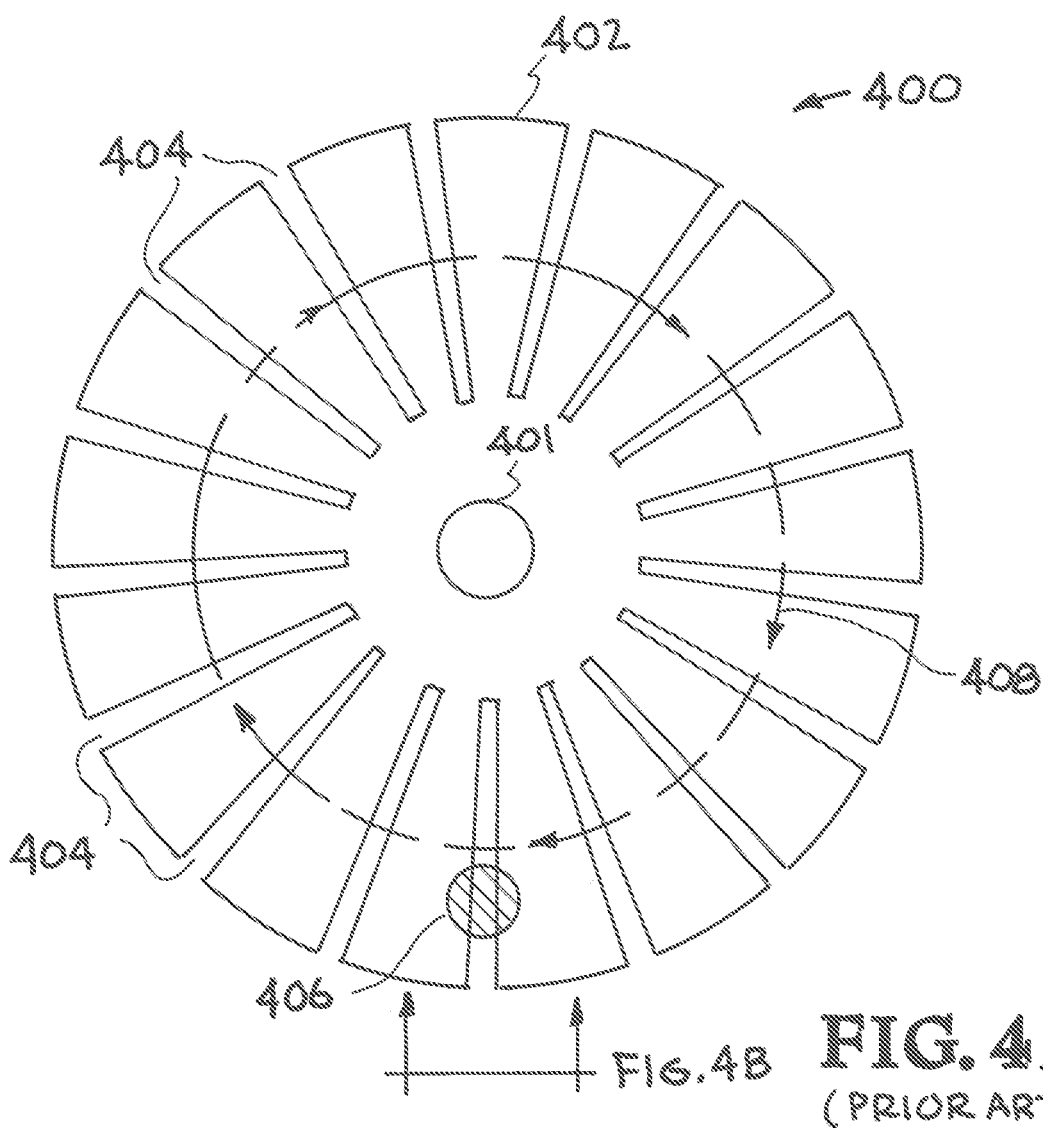
FIG. 4A provides an illustration of prior art for analyzing electron beams wherein the illustration serves as background for the description of the Applicants' new and improved apparatus, systems, and methods.
Figure 4B:
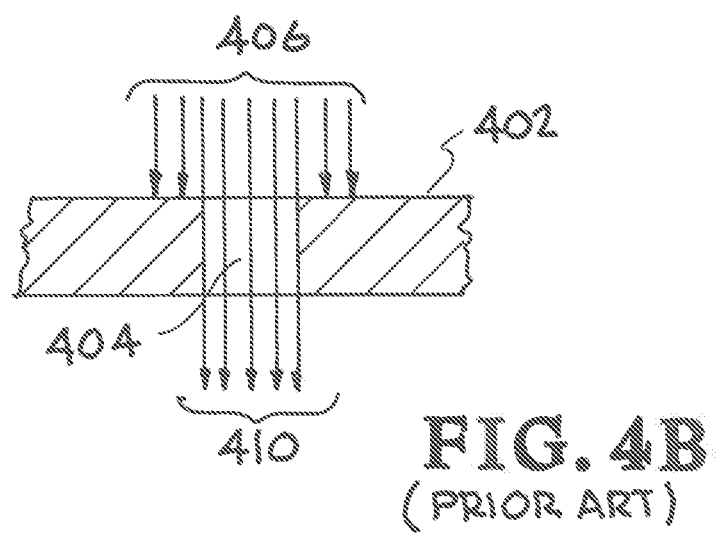
FIG. 4B is a cross-section of the portion in the circle of FIG. 4A wherein the portion provides a more detailed illustration of the system shown in FIG. 4A.

As shown in FIG. 3, the slit 204 extends through the metal disk 202 at an angle 205 to the beam 208. The slit 204 has a width "w". By inclining the slit 204 at the angle 205 the effective slit width is reduced to less than the slit width. The effective slit width is identified by "d" in FIG. 3. Referring now to FIGS. 4A and 4B, information about a prior art system is provided to serve as background for the description of the present invention. The prior art system is designated generally by the reference numeral 400. The prior art system 400 is a 17-slit radial slit disk that is used to profile electron beams using the EMFC, and b) cross section through one of the slits, illustrating how the slit captures a portion of the electron beam during normal operation.

Referring now to FIG. 4A the prior art system 400 includes a refractory metal disk 402, constructed preferably of tungsten, but may be constructed of tantalum, tungsten-rhenium, or other refractory metals. Disk 402 is provided, with a center hole 401 and a number (usually odd) of slits 404 extending radially outward from center hole 401 but spaced from the center hole. The number of slits is restricted by the allowable spacing of the slits. In this embodiment the disk 402 contains seventeen (17) slits. An electron or ion beam 406 travels in circular path 408 around the disc 402 and as the beam 406 crosses the slits 404 a signal is generated. This signal goes to a data acquisition system where an image of the current density in high or low power ion or electron beams is created. The number of data points taken is limited to the spacing of the slots.

FIG. 4B is a cross-section of a section of slit 404 of disk 402 shown in FIG. 4A looking radially downward. FIG. 4B illustrates how the slit 404 captures only a portion of the electron beam 406 during normal operation. The electron or ion beam 406 is wider than the slit 404 and only a portion 410 of the beam 406 passes through slit 404.

As illustrated in FIGS. 4A and 4B, as the electron beam 406 scans over a slit 404 only a portion 410 of the beam passes through the slit 404. As the beam moves over the slit, a fast acting data acquisition system generates a profile of the distribution of current in the beam. By taking profiles over multiple radial slits, CT algorithms are used to calculate the power distribution in the beam.

This method works as long as the beam diameter is several times larger than the slit that is approximately 100 microns wide. Newer machines are generating finer beam diameters. Producing finer slits in refractory metals would have an advantage in that these smaller beams could be analyzed, and the spatial resolution of the CT reconstruction would be improved for all measured beams. However, there is a practical limitation on how fine a slit can be manufactured in a refractory metal disk, and slits smaller than 100 microns tend to be either cost prohibitive or not possible at all. Applicants' apparatus, systems, and methods solves this problem by manufacturing the slits of normal width, but oriented at an angle to the direction of the electron beam that is being measured.

Figure 5:
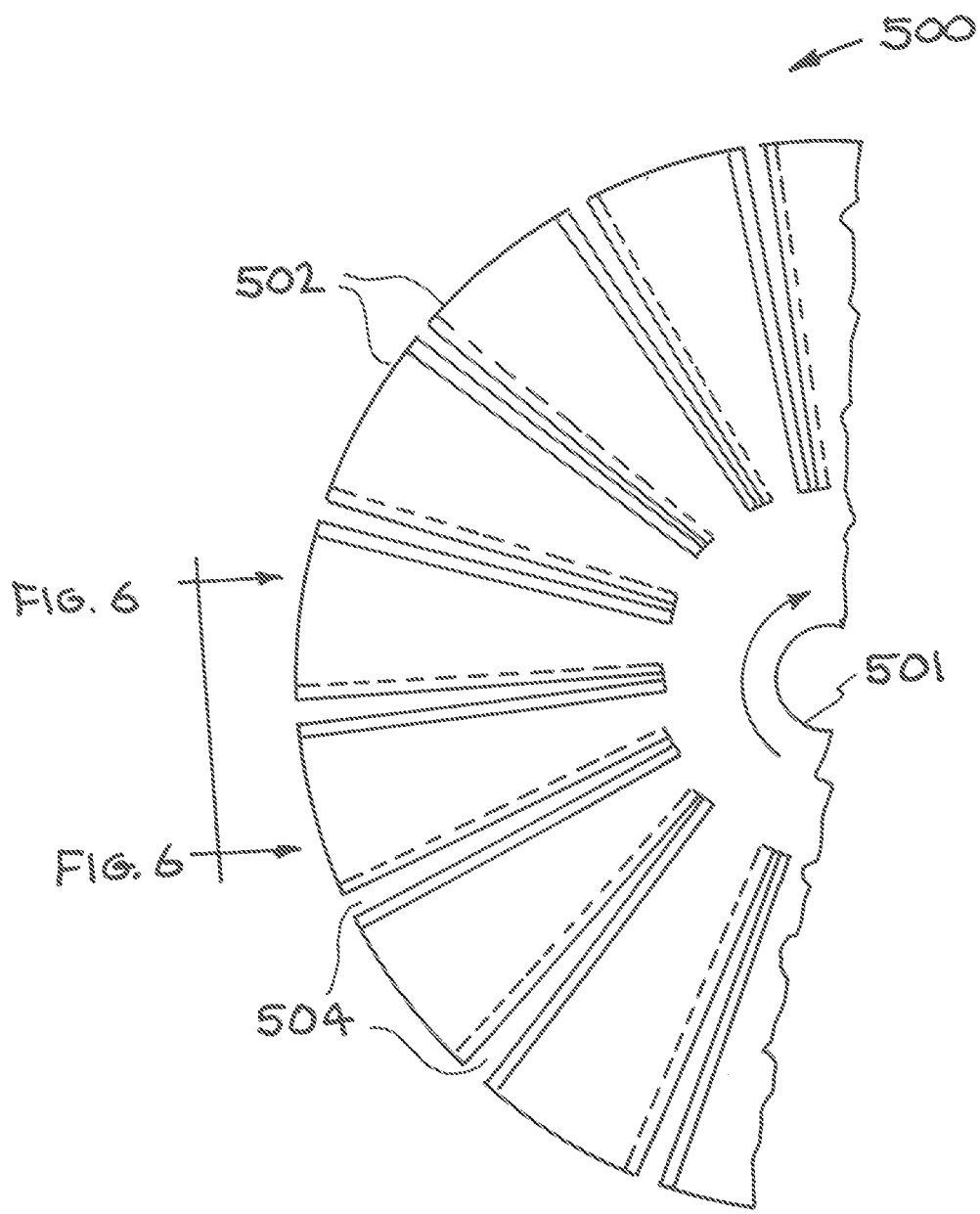
FIG. 5 is a simplified schematic depiction that illustrates a second embodiment of the inventor's apparatus, systems, and methods.

Referring now to FIG. 5, a simplified schematic depiction illustrates a second embodiment of the inventor's apparatus, systems, and methods. This second embodiment is a system for tomographic imaging of large electron beams. This second embodiment is designated generally by the reference numeral 500. As illustrated, the embodiment 500 includes a number of components. The components of the inventor's apparatus, systems, and methods 500 illustrated in FIG. 5 are identified and described below.

Reference Numeral 501—center hole,
Reference Numeral 502—refractory metal disk, and
Reference Numeral 504—slits.

This section provides background information related to the present disclosure which is not necessarily prior art.

The identification and description of the second embodiment 500 components illustrated in FIG. 5 having been completed, the operation and additional description of the inventor's second embodiment 500 will now be considered in greater detail. FIG. 5 provides an illustration of how an angled slit would work for a beam larger than the width of the slit. The refractory metal disk 502 includes a center hole 501 and slits 504 that extend radially outward from center hole 501. The slits 504 are spaced from the center hole 501. By inclining the slits 504 at an angle the effective slit width is reduced to less than the slit width. The inclined slit is further illustrated in FIG. 6. The FIG. 6 view is taken as indicated by the arrows in FIG. 5.

Figure 6:
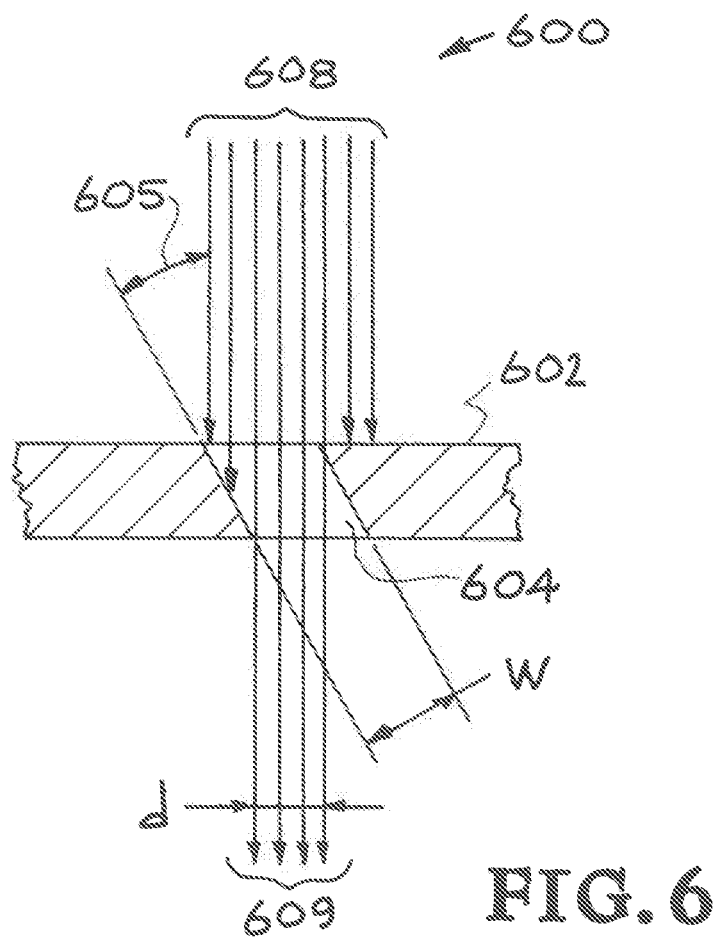
FIG. 6 is a view indicated by the arrows in FIG. 5.

Referring now to FIG. 6, a view taken as indicated by the arrows in FIG. 5 provides an illustration of the second embodiment of the inventors' angled slit. The view in FIG. 6 is an illustration showing the inventors' new angled slit 604 that provides an effective slit width that is smaller than the actual slit 604, allowing for the measurement of beams having larger diameters than the slit width.

A portion of the refractory metal disk 602 is shown in FIG. 6 with a slit 604 extending through the metal disk 603. The slit 604 extends through the metal disk 603 at an angle 605 to the beam 608. By inclining the slit 604 at an angle 605 relative to the direction of the beam's propagation, the effective slit width, d, is reduced to a value less than the slit width, w. The angled slit design works well with beams having larger diameters than the slit width. By inclining the slit 604 at an angle 605 relative to the direction of the beam's propagation, the effective slit width, d, is reduced to a value less than the slit width, w.

Figure 7:
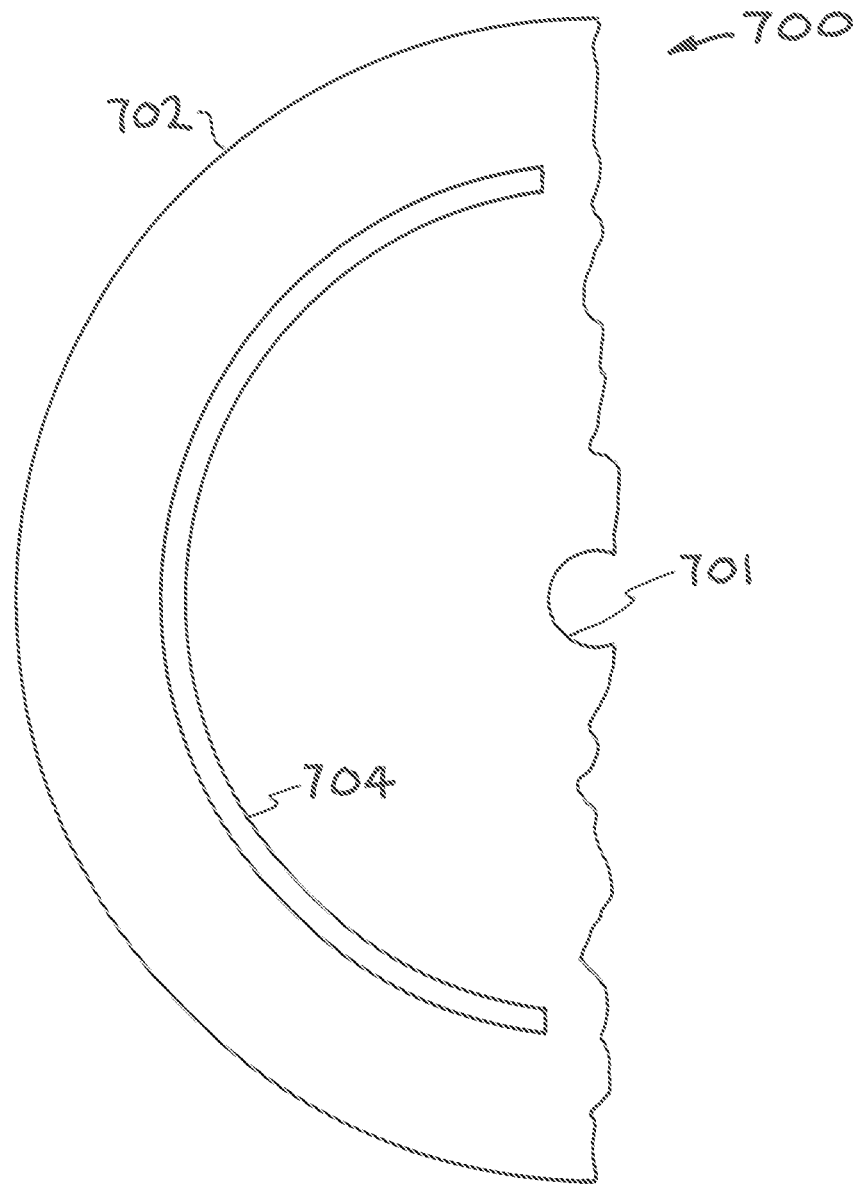
FIGS. 7-9 are simplified schematic depictions that illustrate a third embodiment of the inventor's apparatus, systems, and methods.

Referring now to FIG. 7, a simplified schematic depiction illustrates a third embodiment of the inventor's apparatus, systems, and methods. FIG. 7 is a generalized high level illustration showing a computed tomographic system with an annular slit. The embodiment illustrated in FIG. 7 is designated generally by the reference numeral 700. As illustrated, the embodiment 700 includes a number of components. The components illustrated in FIG. 7 are identified and described below.

Reference Numeral 701—center hole,
Reference Numeral 702—refractory metal disk, and
Reference Numeral 704—annular slit.

The identification and description of the embodiment 700 components illustrated in FIG. 7 having been completed, the operation and additional description of the inventor's third embodiment 700 will now be considered in greater detail. The embodiment 700 has an annular slit 704 which the beam passes through as it is scanned over the slit 704. The slit 704 is formed in refractory metal disk 702. The metal disk 702 is made of high temperature refractory metals such as tungsten. The portion of the beam passing through the slit 704 is intercepted by a Faraday cup arrangement below the slit 704. The acquired signal is processed through a data acquisition system.

Figure 8:
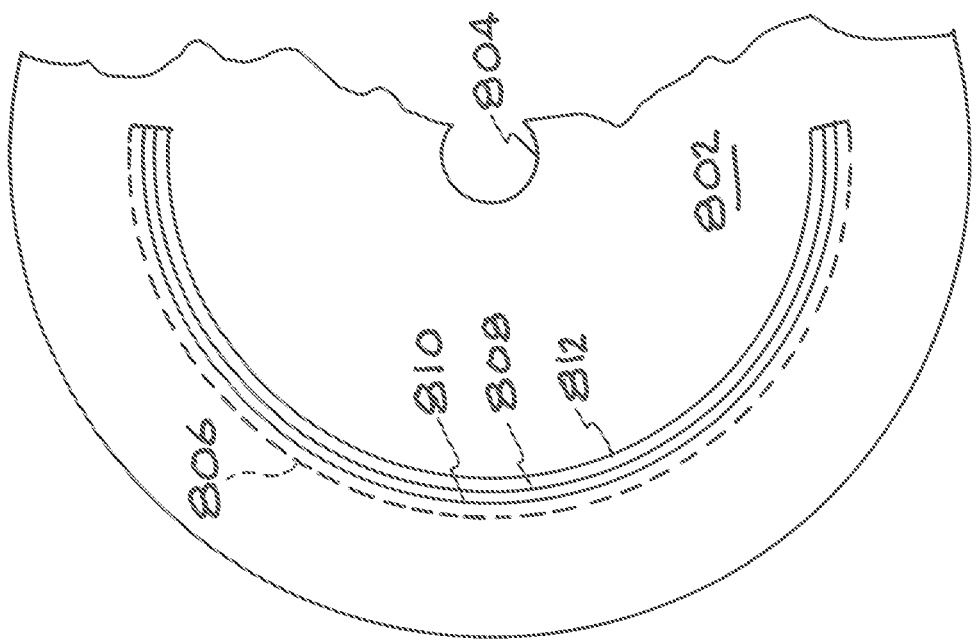

Referring now to FIG. 8, another simplified schematic depiction further illustrates the third embodiment of the inventor's apparatus, systems, and methods. The FIG. 8 depiction includes an annular slit 804. As illustrated, the depiction 800 includes the components identified and described below.

Reference Numeral 802—refractory metal disk,
Reference Numeral 804—center hole,
Reference Numeral 806—first lower slit edge,
Reference Numeral 808—second lower slit edge,
Reference Numeral 810—first upper slit edge, and
Reference Numeral 812—second upper slit edge, The identification and description of the depiction 800 of the third embodiment components illustrated in FIG. 8 having been completed, the operation and additional description of the inventor's third embodiment will now be considered in greater detail. The depiction 800 shows the annular slit which the beam passes through as it is scanned over the annular slit. The slit is formed in refractory metal disk 802. The metal disk 802 is made of high temperature refractory metals such as tungsten. The portion of the beam passing through the slit is intercepted by a Faraday cup arrangement below the slit. The acquired signal is processed through a data acquisition system. The beam is produced by an electron beam source and controller. The centerline of the electron beam is at an angle to the annular slot. That angle is governed by the distance of the electron beam source from the top surface of the refractory metal disk 802. The annular slit of the depiction 800 is made with the annular slit being at an angle to the centerline of the electron beam.

Applicant's annular slit embodiment is complicated by the fact that (1) the annular slot is at an angle to centerline of the electron beam and (2) the slot itself is also at an angle to centerline of the electron beam. As illustrated in FIG. 8, the annular slit has a first lower slit edge 806, a second lower slit edge 808, a first upper slit edge 810, and a second upper slit edge 812.

Figure 9:
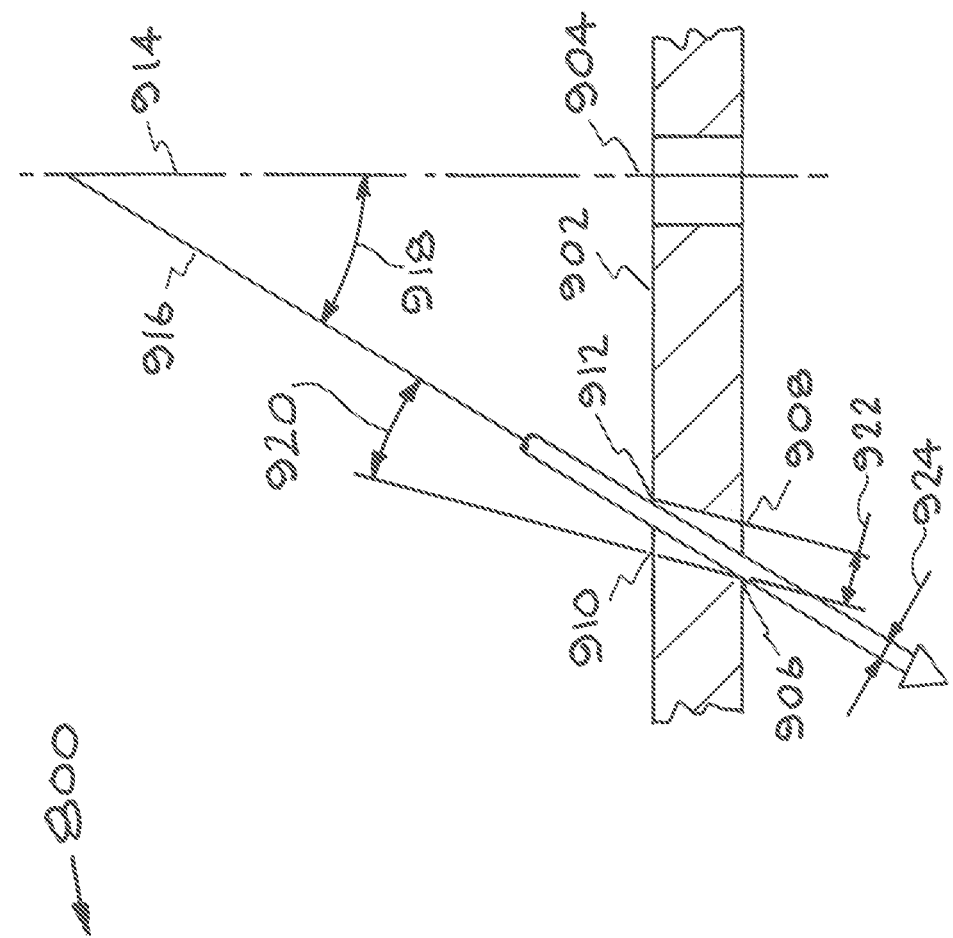

Referring now to FIG. 9, a simplified schematic depiction further illustrates the third embodiment of the inventor's apparatus, systems, and methods in greater detail. This depiction is designated generally by the reference numeral 900. As illustrated, the depiction 900 includes a number of components. The components of the depiction 900 illustrated in FIG. 9 are identified and described below.

Reference Numeral 902—refractory metal disk,
Reference Numeral 904—center hole,
Reference Numeral 906—first lower slit edge,
Reference Numeral 908—second lower slit edge,
Reference Numeral 910—first upper slit edge, and
Reference Numeral 912—second upper slit edge,
Reference Numeral 914—refractory metal disk center line,
Reference Numeral 916—center line of the beam,
Reference Numeral 918—angle of beam to refractory disk center line,
Reference Numeral 920—angle of slit to beam center line,
Reference Numeral 922—width of slit, and
Reference Numeral 924—width of beam.

The identification and description of the depiction 900 components illustrated in FIG. 9 having been completed, the operation and additional description of the depiction 900 will be considered in greater detail. FIG. 9 provides an illustration of how Applicant's angled annular slit would work for an annular slot refractory metal disk 902 wherein the beam center line is at an angle to the refractory metal disk 902.

The refractory metal disk 902 includes a center hole 904, an annular slit that located at fixed annular distance from the center hole 904, and a beam with a width 924 that is at an angle to the refractory metal disk 902. This type of electron beam diagnostic system is shown in U.S. Pat. No. 9,105,448,755 for an electron beam diagnostic system using computed tomography and an annular sensor.

The depiction 900 shows that the annular slot is at an angle 918 to centerline of the refractory metal disk 902. Further, the slot itself is at an angle 920 to the centerline 916 of the electron beam. The annular slit has a width "922". By inclining the annular slit at the angle 920 to the beam centerline 916 the effective slit width is reduced to less than what the slit width would be if the annular slit was parallel to the to the beam centerline 916.

As illustrated in FIG. 9, the annular slit has a first lower slit edge 906, a second lower slit edge 908, a first upper slit edge 910, and a second upper slit edge 912. The beam having a width 924 passes between first upper slit edge 910 and second lower slit edge 908. By inclining the annular slit at the angle 920 to the beam center line 916 the effective slit width is reduced to less than what the slit width would be if the annular slit was parallel to the to the beam center line 916.

The inventors' apparatus, systems, and methods provide a new angled slit design whereby the slit walls are not oriented parallel to the electron beam being measured, but instead are oriented at an angle to the electron beam. The inventors' new angled slit utilizes the steps of providing an electron or ion beam, wherein the beam has a beam axis; providing a refractory metal disk; providing at least one slit in the refractory metal disk that receives the beam, wherein the slit is at an angle to the beam axis; providing a beam entrance opening in the slit that allows the beam to enter; providing an effective beam exit opening in the slit that allows the beam to exit, wherein the beam effective exit opening is smaller than the beam entrance opening; moving the beam across the refractory metal disk, wherein the beam enters the slit through the beam entrance opening and exits the slit through the effective beam exit opening; and using a computed tomographic device for measuring the beam that enters and exits the slit for analyzing the beam.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A computed tomographic apparatus, comprising:
    an electron or ion beam, wherein said beam has a beam axis;
    a refractory metal disk;
    a multiplicity of slits in said refractory metal disk that receive said beam, wherein said slits are at an angle to said beam axis;
    beam entrance openings in said slits that allow said beam to enter;
    effective beam exit openings in said slits that allow said beam to exit, wherein said beam effective exit openings are smaller than said beam entrance openings;
    a system for moving said beam across said refractory metal disk, wherein said beam enters said slits through said beam entrance openings and exits said slits through said effective beam exit openings; and
    a computed tomographic device for measuring said beam that enters and exits said slits for analyzing said beam.

2. The computed tomographic apparatus for analyzing an electron or ion beam of claim 1 wherein said beam has a beam diameter that is smaller than said beam entrance openings.

3. The computed tomographic apparatus for analyzing an electron or ion beam of claim 1 wherein said beam has a beam diameter that is larger than said beam entrance openings.

4. The computed tomographic apparatus for analyzing an electron or ion beam of claim 1 wherein said beam has a beam diameter that is the same size as said beam entrance openings.

5. The computed tomographic apparatus for analyzing an electron or ion beam of claim 1 wherein said multiplicity of slits in said refractory metal disk are radial slits.

6. The computed tomographic apparatus for analyzing an electron or ion beam of claim 1 wherein said multiplicity of slits in said refractory metal disk are annular slits.

7. A computed tomographic method, comprising the steps of:
    providing an electron or ion beam, wherein said beam has a beam axis;
    providing a refractory metal disk;
    providing a multiplicity of slits in said refractory metal disk that receive said beam, wherein said slits are at an angle to said beam axis;
    providing beam entrance openings in said slits that allow said beam to enter;
    providing effective beam exit openings in said slits that allow said beam to exit, wherein said beam effective exit openings are smaller than said beam entrance openings;
    moving said beam across said refractory metal disk, wherein said beam enters said slits through said beam entrance openings and exits said slits through said effective beam exit openings; and
    using a computed tomographic device for measuring said beam that enters and exits said slits for analyzing said beam.

8. The computed tomographic apparatus for analyzing an electron or ion beam of claim 7 wherein said beam has a beam diameter that is smaller than said beam entrance openings.

9. The computed tomographic apparatus for analyzing an electron or ion beam of claim 7 wherein said beam has a beam diameter that is larger than said beam entrance openings.

10. The computed tomographic apparatus for analyzing an electron or ion beam of claim 7 wherein said beam has a beam diameter that is the same size as said beam entrance openings.

11. The computed tomographic apparatus for analyzing an electron or ion beam of claim 7 wherein said multiplicity of slits in said refractory metal disk are radial slits.

12. The computed tomographic apparatus for analyzing an electron or ion beam of claim 7 wherein said multiplicity of slits in said refractory metal disk are annular slits.

13. A computed tomographic apparatus, comprising:
    an electron or ion beam, wherein said beam has a beam axis;
    a refractory metal disk;
    a multiplicity of radial slits in said refractory metal disk that receive said beam, wherein said radial slits are at an angle to said beam axis;
    beam entrance openings in said radial slits that allow said beam to enter;
    effective beam exit openings in said radial slits that allow said beam to exit, wherein said beam effective exit openings are smaller than said beam entrance openings;
    a system for moving said beam across said refractory metal disk, wherein said beam enters said radial slits through said beam entrance openings and exits said radial slits through said effective beam exit openings; and a computed tomographic device for measuring said beam that enters and exits said radial slits for analyzing said beam.

14. The computed tomographic apparatus for analyzing an electron or ion beam of claim 13 wherein said beam has a beam diameter that is smaller than said beam entrance openings.

15. The computed tomographic apparatus for analyzing an electron or ion beam of claim 13 wherein said beam has a beam diameter that is larger than said beam entrance openings.

16. The computed tomographic apparatus for analyzing an electron or ion beam of claim 13 wherein said beam has a beam diameter that is the same size as said beam entrance openings.

17. A computed tomographic apparatus, comprising:
   an electron or ion beam, wherein said beam has a beam axis;
   a refractory metal disk;
   at least one annular slit in said refractory metal disk that receives said beam, wherein said slit is at an angle to said beam;
   a beam entrance opening in said slit that allows said beam to enter;
   an effective beam exit opening in said slit that allow said beam to exit, wherein said beam effective exit opening is smaller than said beam entrance opening;
   a system for moving said beam on said refractory metal disk, wherein said beam enters said slit through said beam entrance opening and exits said slit through said effective beam exit opening; and
   a computed tomographic device for measuring said beam that enters and exits said slit for analyzing said beam.

18. The computed tomographic apparatus for analyzing an electron or ion beam of claim 17 wherein said beam has a beam diameter that is smaller than said beam entrance opening.

19. The computed tomographic apparatus for analyzing an electron or ion beam of claim 17 wherein said beam has a beam diameter that is larger than said beam entrance opening.

20. The computed tomographic apparatus for analyzing an electron or ion beam of claim 17 wherein said beam has a beam diameter that is the same size as said beam entrance opening.

* * * * *